(12) United States Patent
Cakic et al.

(10) Patent No.: US 12,357,286 B2
(45) Date of Patent: Jul. 15, 2025

(54) TOOL FOR THE SUBCUTANEOUS CUTTING OF TENDONS

(71) Applicant: MEDACTA INTERNATIONAL SA, Castel San Pietro (CH)

(72) Inventors: Luka Cakic, Castel San Pietro (CH); Francesco Siccardi, Castel San Pietro (CH); Sascha Berberich, Castel San Pietro (CH); Riccardo Lucchini, Castel San Pietro (CH); Gianluca Parisi, Castel San Pietro (CH)

(73) Assignee: Medacta International SA, Castel San Pietro (CH)

( * ) Notice: Subject to any disclaimer, the term of this patent is extended or adjusted under 35 U.S.C. 154(b) by 776 days.

(21) Appl. No.: 17/276,034

(22) PCT Filed: Aug. 22, 2019

(86) PCT No.: PCT/IB2019/057067
§ 371 (c)(1),
(2) Date: Mar. 12, 2021

(87) PCT Pub. No.: WO2020/053685
PCT Pub. Date: Mar. 19, 2020

(65) Prior Publication Data
US 2022/0047254 A1 Feb. 17, 2022

(30) Foreign Application Priority Data

Sep. 13, 2018 (IT) .......................... 102018000008564

(51) Int. Cl.
*A61B 17/00* (2006.01)
*A61B 17/3209* (2006.01)

(52) U.S. Cl.
CPC .... *A61B 17/00008* (2013.01); *A61B 17/3209* (2013.01); *A61B 2017/00455* (2013.01); *A61B 2017/00969* (2013.01)

(58) Field of Classification Search
CPC .......... A61B 17/00008; A61B 17/3209; A61B 2017/00455; A61B 2017/00969; A61B 2017/0046; A61B 17/320016
See application file for complete search history.

(56) References Cited

U.S. PATENT DOCUMENTS 2,316,297 A * 4/1943 Southerland ..... A61B 17/12013
606/139
5,366,476 A * 11/1994 Noda ................. A61B 17/2909
606/41

(Continued)

FOREIGN PATENT DOCUMENTS

DE 4123839 A1 2/1992
DE 9214580 U1 3/1994

(Continued)

OTHER PUBLICATIONS

Notice of Reasons for Refusal, dated May 31, 2022, received in connection with corresponding JP Patent Application No. 2021-514084, with English translation, 11 pages.

(Continued)

*Primary Examiner* — Ashley L Fishback
(74) *Attorney, Agent, or Firm* — Meunier Carlin & Curfman LLC

(57) ABSTRACT

Various implementations include a tool for the subcutaneous cutting of tendons. The tool includes a shaft, arranged along a longitudinal axis, having a proximal end and a distal end, a grip, provided at the proximal end, comprising a fixed handle and a movable trigger, and a cutting head placed at the distal end, which comprises a tendon harvesting tip provided with a groove and a blade. The blade and the (Continued)

harvesting tip are movable relative to each other on a plane which contains the longitudinal axis of the shaft. The blade is inclined with respect to the longitudinal axis of said shaft.

12 Claims, 5 Drawing Sheets

(56) References Cited

U.S. PATENT DOCUMENTS

| | | | |
|---|---|---|---|
| 6,117,152 A * | 9/2000 | Huitema | A61B 17/320092 |
| | | | 601/2 |
| 6,254,620 B1 | 7/2001 | Koh et al. | |
| 2012/0283793 A1* | 11/2012 | Burroughs, III | A61B 17/1767 |
| | | | 606/86 R |
| 2014/0277020 A1* | 9/2014 | Koogle | A61B 17/320016 |
| | | | 606/167 |
| 2018/0014821 A1 | 1/2018 | Weber et al. | |
| 2019/0201035 A1* | 7/2019 | Amirouche | A61B 17/00008 |

FOREIGN PATENT DOCUMENTS

| | | | | |
|---|---|---|---|---|
| DE | 9214580 | * | 4/1994 | ......... A61B 17/0467 |
| JP | 2012502688 A | | 2/2012 | |
| JP | 2012510350 A | | 5/2012 | |
| JP | 2014527424 A | | 10/2014 | |
| WO | WO-2006096805 A1 | * | 9/2006 | ......... A61B 17/0467 |
| WO | 2010030872 A2 | | 3/2010 | |
| WO | 2010065707 A2 | | 6/2010 | |
| WO | 2013009576 A1 | | 1/2013 | |

OTHER PUBLICATIONS

International Search Report and Written Opinion for International Application No. PCT/IB2019/057067 dated Nov. 15, 2019, 12 pages.

* cited by examiner

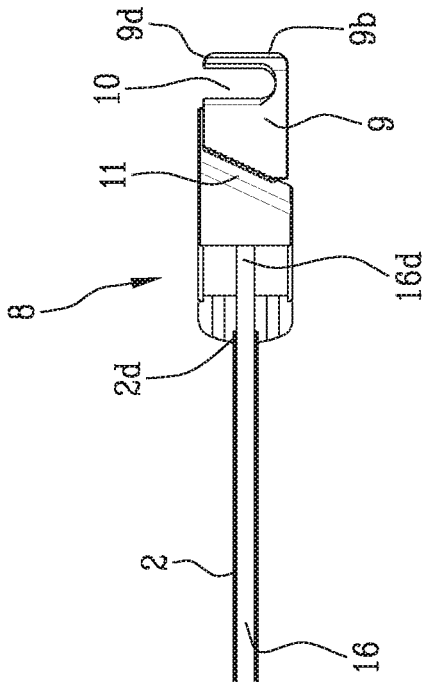
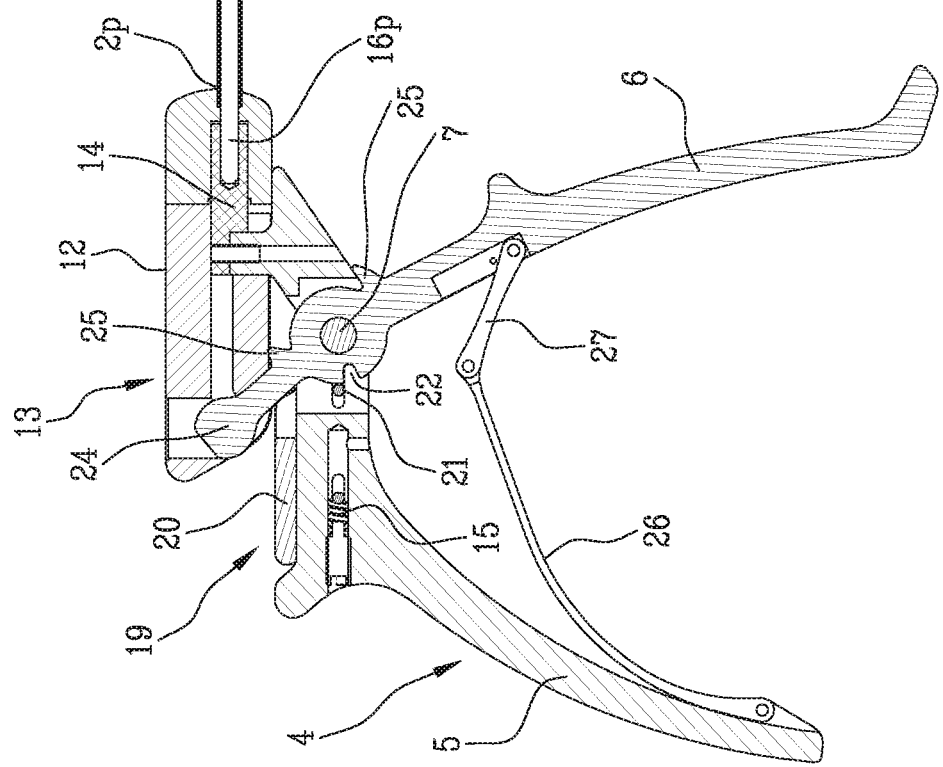
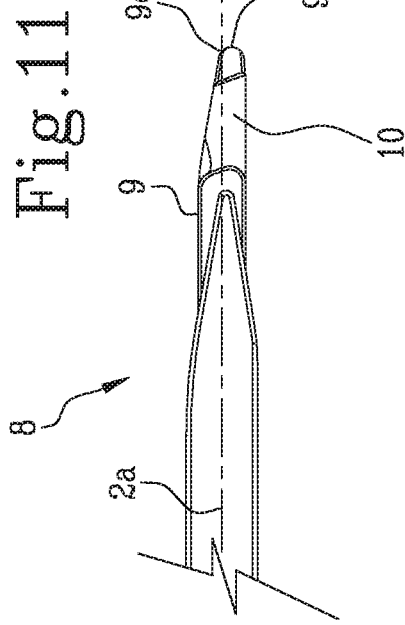

TOOL FOR THE SUBCUTANEOUS CUTTING OF TENDONS

TECHNICAL FIELD

The present invention relates to a tool for the subcutaneous cutting of tendons.

PRIOR ART

The cutting tool that is the subject of the present invention is intended for the subcutaneous cutting of the quadriceps tendon, which, as is well known, offers significant benefits for the reconstruction of the cruciate ligament.

In particular, this cutting tool is used to sever the proximal end of the tendon.

The quadriceps tendon can attain a larger diameter than others, its harvest site has a low morbidity with respect to e.g. the patellar tendon, it has good biomechanical properties and, since it is less prone to strain or deformation, it has a stiffness profile that is preferable for the reconstruction of the knee ligament.

The surgical technique for cutting and removing the quadriceps tendon involves a cutaneous incision above the upper edge of the patella.

After the subcutaneous dissection, the layers of the prepatellar bursa are longitudinally separated to expose the quadriceps tendon.

Then the tendon is incised with a vertical cutting tool, or tendon strippers, of the desired width for the reconstruction of the cruciate ligament.

Through the cutaneous incision, the cutting tool for the vertical incision is applied to the tendon in a subcutaneous position and pushed proximally onto the tendon until it reaches the desired length for the transplant. Thus, the tendon is not completely severed but incised at the sides.

A second step of the operation involves horizontally cutting the tendon, parallel to the axis of extension of the tendon itself. With this step, the portion of the tendon to be removed is separated above and below from the surrounding soft tissue, by means of a second cutting tool, for example a cutting tool for horizontal incision. This cutting tool for horizontal incision, also known as a tendon separator, defines the thickness of the tendon that has to be removed.

Through the cutaneous incision, the cutting tool for horizontal incision or the tendon separator is introduced laterally into the incision of the tendon and subcutaneously pushed along the same length in the proximal direction to horizontally cut the tendon, above and below, along the tendon's direction of extension.

A third stage involves the insertion, again subcutaneously, of a third tool adapted to transversely sever the proximal end of the tendon, where "proximal" refers to the patient.

Finally, the distal end of the tendon is also transected, and then removed and prepared for use in reconstructing the cruciate ligament.

Specifically, the present invention is related to a tool for the subcutaneous cutting of tendons and, therefore, pertains to the cutting tool used in the third part of the operation.

The known surgical techniques require an open surgical procedure and the tools used make the process of harvesting the tendon itself difficult.

Although some of the most modern techniques offer subcutaneous solutions, they still present difficulties because of the design of and the methods for using the tool.

In some of the most modern techniques, the cutting tool used to sever the proximal end of the tendon has a closed eyelet inside of which the tendon itself is inserted. Therefore, it is necessary to initially sever the distal end of the tendon—the end attached to the patellar bone—which is then inserted inside of the eyelet.

The served distal end is then tied with suture thread, so as to maintain its compact structure and to enable the tool intended for cutting the tendon to engage said severed head in the proximal position and, thus, to complete the harvest of the tendon. In this way, however, the cut is uncontrolled since the removal of the tendon from the patella, an operation which is usually performed freehand with a scalpel, is not guided. Moreover, in order to cut the proximal end of the tendon, the end connected to the quadriceps—the distal end that is already severed—must be held by a suitable tool to keep the tendon in tension; otherwise, the tendon would tend to contract on itself. This involves the risk of damage to the tendon tissue and is also impractical when performing the final operation of the proximal cutting.

Therefore, some of the disadvantages found in the tools currently used include the inevitability of inaccurate cutting and uncontrolled harvest. Other tools, on the other hand, have cutting heads with greater resistance to cutting due to the geometry or structure of the blade itself, which entails the need for repeated cutting actions on the tendon itself, with the consequent risks of damaging the tendon itself.

The purpose of the present invention is to present a tool for the subcutaneous cutting of tendons that overcomes the drawbacks of the prior art described above.

One purpose of the present invention is, in fact, to provide a tool for the subcutaneous cutting of tendons that is minimally invasive and that guarantees the patient a completely safe cut and without any damage to the surrounding soft tissue, nor to the tendon itself.

In addition, the purpose of this invention is to provide a tool for the subcutaneous cutting of tendons that is easy for the surgeon to use and that avoids his/her accidentally cutting the tendon.

Another purpose of the present invention is to provide a tool for the subcutaneous cutting of tendons that enables a fast, safe, steady and precise cut, despite the surgical site's not providing the surgeon with good visibility.

Another purpose of the present invention is to provide a tool for the subcutaneous cutting of tendons that enables an easy process for harvesting the tendon itself as well as preserving the cosmetic aspect after surgery.

These and other purposes are substantially attained by a tool for the subcutaneous cutting of tendons as described in one or more of the accompanying claims.

SUMMARY

In particular, according to a first aspect, the present invention concerns a tool for the subcutaneous cutting of tendons.

Preferably, a shaft is provided, which is arranged along a longitudinal axis, having a proximal end and a distal end, a grip, provided at the proximal end, comprising a fixed handle and a movable trigger, and a cutting head placed at the distal end.

The cutting head preferably comprises a blade and a tendon harvesting tip provided with a groove.

The blade and the harvesting tip are, preferably, movable relative to each other on a plane that contains the longitudinal axis of the shaft.

The cutting head advantageously comprises a blade inclined with respect to the longitudinal axis of the shaft.

The blade is preferably notched.

The blade is preferably slidably movable with respect to the tendon harvesting tip.

The shaft is preferably integrally connected at its distal end to the blade and at its proximal end to a first outer connector.

The first outer connector, the shaft, and the blade preferably form an outer movable system.

The movable trigger is preferably connected to the first outer connector to activate the outer movable system translationally and to move the blade relatively with respect to the tendon harvesting tip.

A shaft is preferably placed axially inside the shaft and is interposed between the grip and the cutting head.

The shaft is preferably connected at one of its distal ends to the harvesting tip and at one of its proximal ends to a second inner connector, connected to the fixed handle of the grip.

The blade preferably has a protrusion at one of its ends, adapted to close the groove of the harvesting tip while cutting the tendon.

The cutting tool preferably comprises a safety device for locking the relative position between the harvesting tip and the blade.

The safety device preferably comprises a locking slider that can slide on the grip, which has a tooth that can engage a groove provided on the trigger.

The locking slider is preferably loaded by a spring.

The trigger is preferably connected rotationally to the fixed handle of the grip by means of a fixing joint.

The shaft preferably has an outer graduated scale for controlling the depth of the subcutaneous insertion of the tool.

The harvesting tip preferably has a tapered plan profile.

BRIEF DESCRIPTION OF THE DRAWINGS

The present invention will be made clearer by the following detailed description, with reference to the attached drawings provided by way of example only, wherein:

FIG. 10 shows a sectioned view of the tool that is the subject of the present invention, as represented in FIG. 1;

FIG. 11 shows a plan view from above of a portion of the tool, in particular of the cutting head.

DETAILED DESCRIPTION

Figure 1:
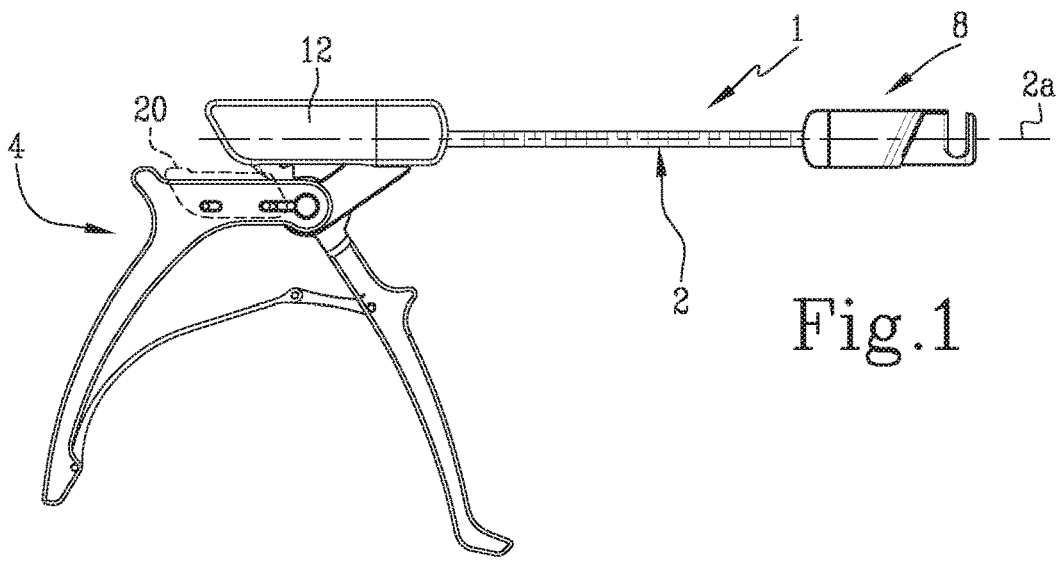
FIG. 1 shows a lateral view of a tool for subcutaneous cutting of tendons in accordance with the present invention, in a first operating configuration.

In the above figures, the number 1 designates in its entirety a tool for the subcutaneous cutting of tendons, according to the present invention.

In the example shown, the tool 1 is suitable for use while performing surgery wherein the quadriceps tendon is removed from its anatomical site to be implanted at another site for reconstructing the cruciate ligament.

In particular, the cutting tool 1 that is the subject of the present invention is used for severing the proximal end of the tendon, the end, that is, that is connected to the quadriceps, where proximal refers to the patient.

The cutting tool 1 comprises a shaft 2, arranged along a longitudinal axis 2a, having a proximal end 2p and a distal end 2d.

The shaft 2 is axially hollow and has on the outer lateral surface 2c a graduated scale 3 that indicates to the surgeon the subcutaneous insertion depth of the tool 1.

The cutting tool 1 also comprises a grip 4, provided at the proximal end 2p of the shaft, which comprises a fixed handle 5 and a movable trigger 6.

The trigger 6 is connected to the fixed handle 5 by means of a connection joint 7 that acts as a fulcrum for the leverage provided by the trigger 6.

The cutting tool 1 also comprises a cutting head 8 placed at the distal end 2d of the shaft 2. The cutting head 8 comprises a tendon harvesting tip 9 provided with a groove 10, and a blade 11.

As can be seen in the attached figures, the groove 10 of the harvesting tip 9 is a U-shaped notch made in the harvesting tip 9. This groove 10 has, therefore, an edge 10b open to the outside.

Figure 4:
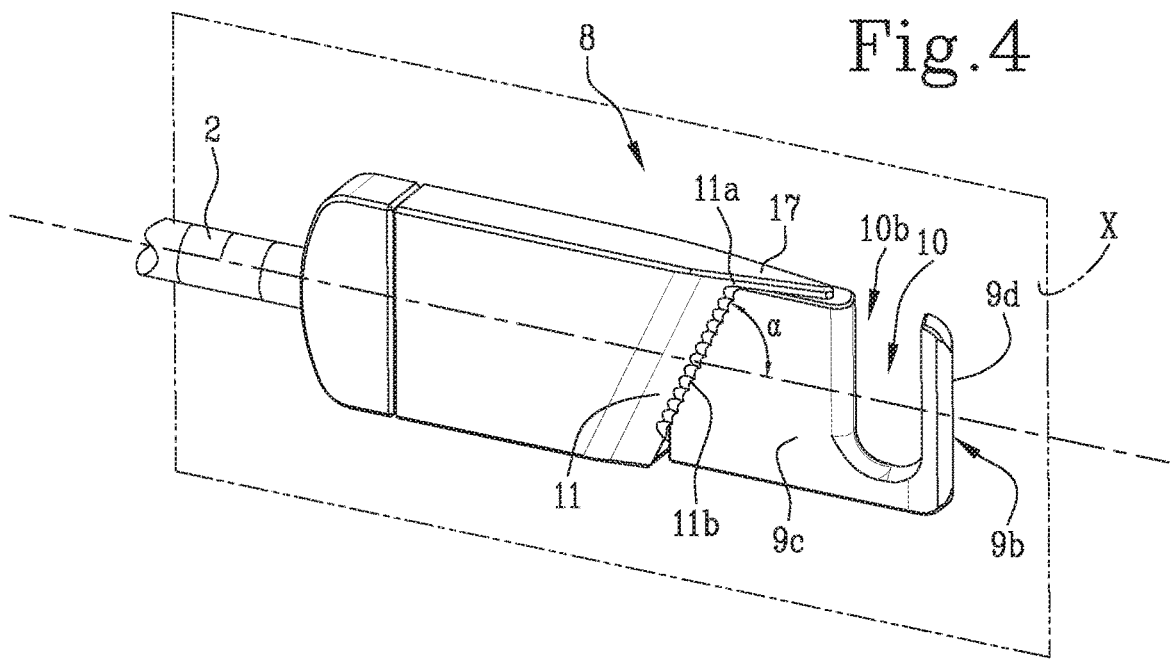
FIG. 4 is a prospective view of a portion of the cutting tool that is the subject of the present invention, in the first operating configuration as shown in FIG. 1.
Figure 8:
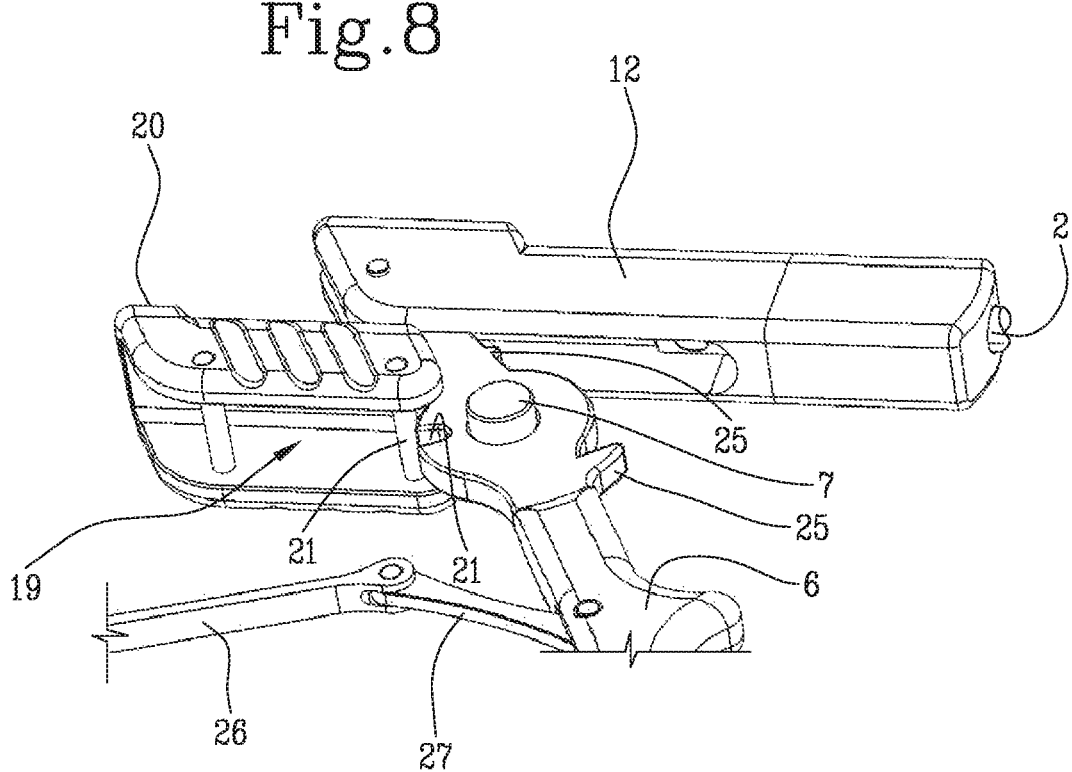
FIG. 8 is a detail of the cutting tool in an unlocking configuration.

As can be seen in FIG. 4, the harvesting tip 9 has, at one of its distal ends 9d, a finger 9b that delimits one side of the groove 10 and that facilitates the gripping of the tendon. As shown in FIG. 8, which shows a plan view from above of the harvesting tip 9, the lateral profile of the harvesting tip 9 is tapered, with respect to the longitudinal axis 2a, to facilitate the insertion of the tool below the tendon and to guide the tendon itself to settle inside the groove 10.

The outer edge of the finger 9b, i.e. the edge of the distal end 9d of the harvesting tip 9, has a rounded profile to prevent soft tissue trauma when inserting the tool.

The blade 11 and the harvesting tip 9 slide relative to each other on a plane X containing the longitudinal axis 2a of the shaft 2, and which is the median plane of symmetry of the cutting tool 1 itself.

Advantageously, it is the blade 11 that is slidably movable with respect to the harvesting tip 9, following the movement of the shaft 2, as will be explained below.

As can be seen in the figures, the blade 11 is inclined with respect to the longitudinal axis 2a of the shaft 2, preferably at an angle of a from 30° to 70°.

Advantageously, the cutting edge 11b of the blade 11 is notched, to obtain a better cutting capacity of the tendon.

The blade 11 has, at one of its ends 11a, a protrusion 17 that, following the relative sliding between the blade 11 and the harvesting tip 9, closes the open edge 10b of the groove 10 by defining an eyelet 18, so as to prevent the tendon, once engaged inside the groove 10, from slipping out of the eyelet 18 thus made.

The shaft 2 is integrally connected to the blade 11 at its distal end 2d and to a first outer connector 12 at its proximal end 2p.

The first outer connector 12, the shaft 2, and the blade 11 form an outer movable system 13.

The first outer connector 12 is, in turn, connected to the movable trigger 6 which acts on the first outer connector 12 to activate the outer movable system translationally along the longitudinal axis 2a of the shaft 2 and to move the blade 11 relatively with respect to the harvesting tip 9 of the tendon.

Connected to the fixed handle 5 of the grip 4, by means of an inner second connector 14 contained inside the first outer connector 12, there is a shaft 16.

This shaft 16 is placed axially inside the shaft 2 which can slide axially on it.

The shaft 16 is interposed between the grip 4 and the cutting head 8. In particular, the shaft 16 is connected at one of its distal ends 16d to the harvesting tip 9 of the tendon and at one of its proximal ends 16p to the second inner connector 14, connected to the fixed handle 5 of the grip 4.

The cutting tool 1 also comprises a safety device 19 adapted to locking the relative position between the harvesting tip 9 and the blade 11 in a certain operating configuration, as described below.

Figure 9:
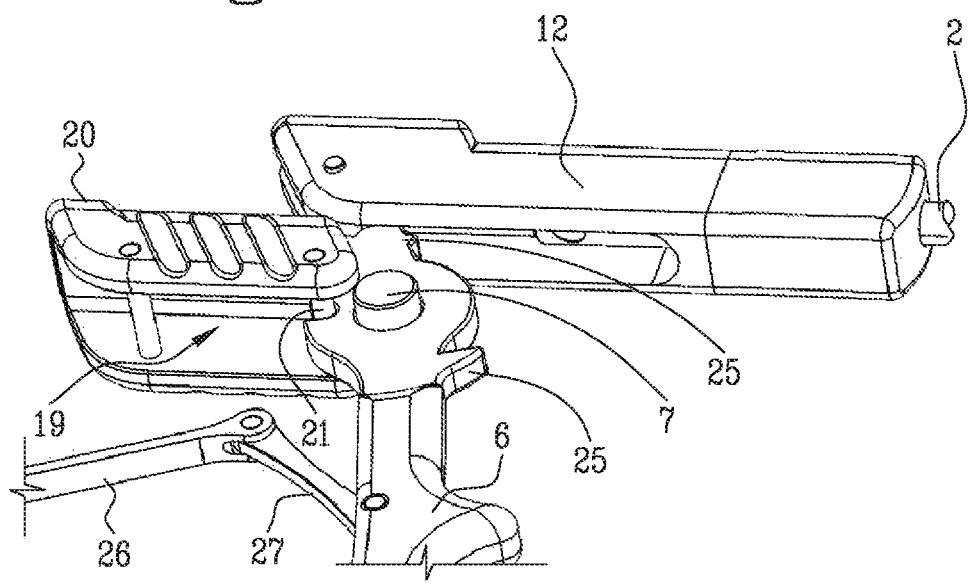
FIG. 9 is the detail shown in FIG. 8 in a locking configuration.

This safety device 19 comprises a locking slider 20, sliding on the grip 4 (FIGS. 8-10).

The locking slider 20 has a tooth 21 that can engage a locking slot 22 provided on the trigger 6 (FIGS. 8-10).

The locking slider 20 is spring-loaded 15 (FIG. 10), which tends to push the slider 20 towards the trigger 6. When the trigger 6 is in a certain position, where the locking slot 22 is aligned with the tooth 21, the latter engages inside the slot preventing the rotation of the trigger 6 and therefore the activation of the outer movable system 13 that drives the blade 11.

The geometric interference between the tooth 21 of the locking slider 20 and the locking slot 22, which is on one side of the trigger 6, prevents rotation of the trigger 6 in either the opening or closing direction.

The trigger 6 engages with the first outer connector 12 by means of a portion 24 placed above the connection joint 7.

The portion 24 of the trigger 6 mechanically interferes with the first outer connector 12, preferably at a proximal end of the connector itself. More specifically, a possible embodiment can involve said lobed portion 24, as shown in FIG. 10, which engages the first outer connector 12 to push it in the distal direction. Alternatively, a portion 24 equipped with a slot can be provided, inside of which a pin, which is inside the first outer connector 12, is engaged. Other solutions may however be envisaged to cause the interaction between the trigger 6 and first outer connector 12 and the axial sliding of the latter following the rotation of the trigger around the connection joint 7.

The trigger 6 also comprises two projections 25 that act as the end stops at the maximum and minimum points of the trigger's movement.

The grip 4 of the cutting tool 1 is spring-loaded by the interconnection between a spring 26 and a lever 27 interposed between the fixed handle 5 and the trigger 6.

This enables the instrument to return to its open configuration after pressure is applied to the trigger 6 to bring it closer to the fixed handle 5 and to provide a feeling of resistance when using the instrument to calibrate the surgeon's pressure on the grip 4.

Figure 2:
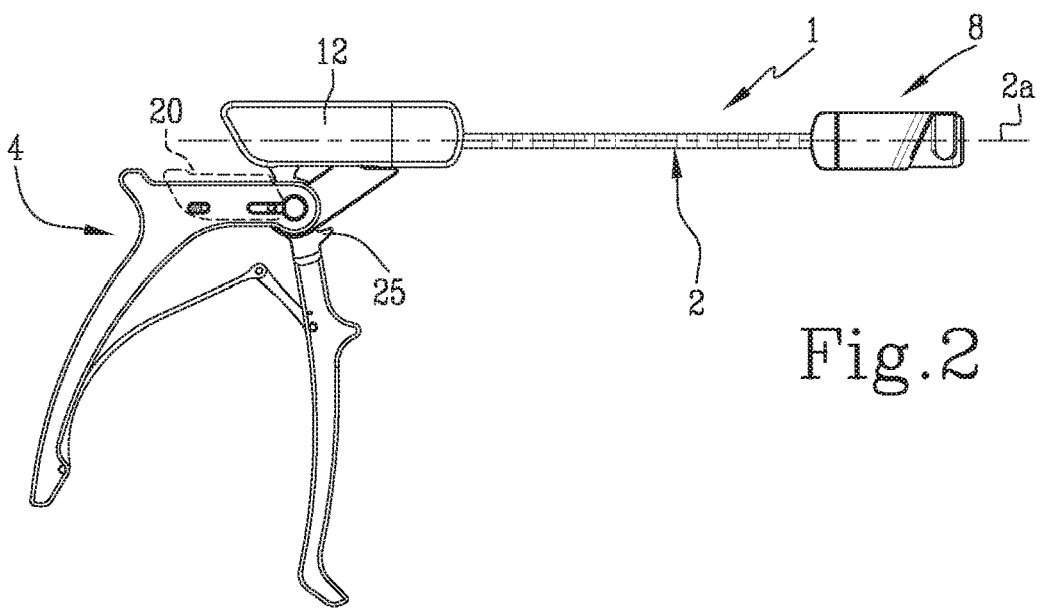
FIG. 2 shows a lateral view of the tool for subcutaneous cutting of tendons in accordance with the present invention, in a second operating configuration.
Figure 3:
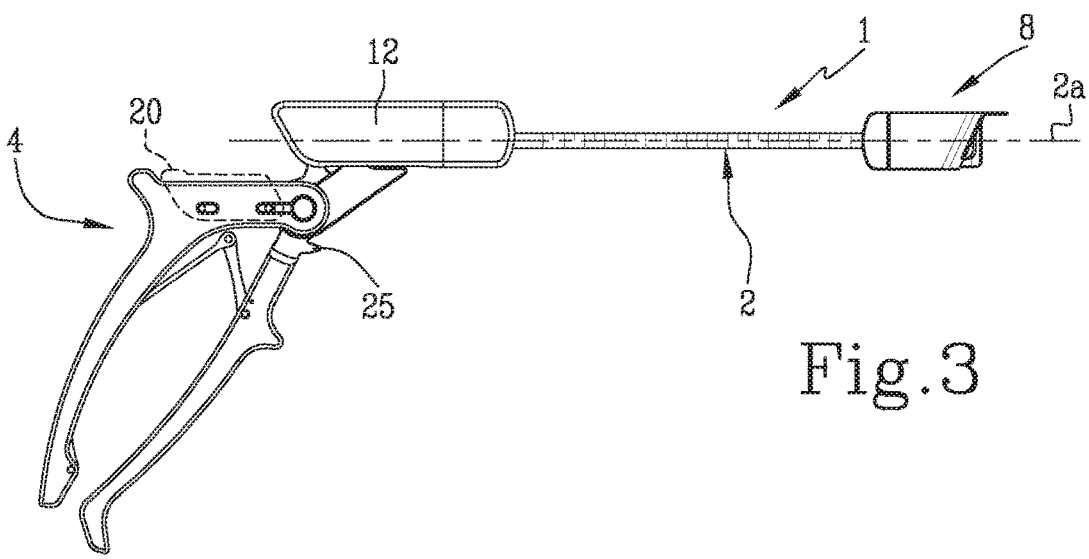
FIG. 3 shows a lateral view of the tool for subcutaneous cutting of tendons in accordance with the present invention, in a third operating configuration.

The cutting tool 1 has three operating configurations: a first configuration for subcutaneously inserting the tool (FIG. 1), a second configuration for tendon locking and tool advancement (FIG. 2), and a third configuration for tendon cutting (FIG. 3).

In the first configuration, the harvesting tip 9 takes the form shown in FIGS. 1 and 4, thus, with the groove 10 fully open.

The tendon is inserted inside the groove 10 of the harvesting tip 9.

In this configuration, the grip 4 is completely separated, i.e. the trigger 6 is at the maximum distance from the fixed handle 5 as a result of the action exerted by the spring 26 and by the lever 27 interposed between the fixed handle 5 and the trigger 6.

The locking slider 20 is in the retracted or proximal position, i.e. completely towards the fixed handle 4, as the locking slot 22 of the trigger 6 is not aligned with the tooth 21 of the slider 20.

If the surgeon does not exert any pressure on the trigger 6, the blade 11 does not move and remains protected against a lateral wall 9c of the harvesting tip 9, preventing the cutting of the tendon since the cutting edge 11b is not exposed.

Once the tendon is inserted inside the groove 10 of the harvesting tip 9, the tool is advanced. For subcutaneous advancement of the tool, the tendon must be locked inside the groove 10 of the grooved tip 9. The tool is then taken to the second configuration, shown in FIGS. 2 and 5.

Figure 5:
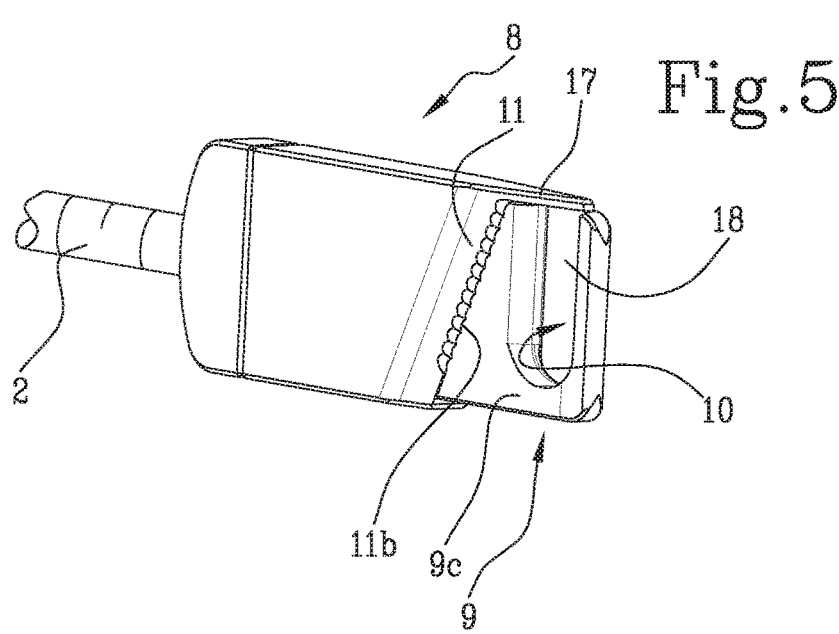
FIG. 5 is a perspective view of the portion of the cutting tool shown in FIG. 4, in the second operating configuration as shown in FIG. 2.

To bring the tool into its second configuration, the surgeon presses the lever of the trigger 6 by a fixed amount (i.e. by closing the handle): with this action, the trigger 6 rotates around the fixing joint 7, which acts as the fulcrum, thus obtaining the sliding of the components of the outer movable system 13 and, thus, the translatory movement of the cutting blade 11 in its tendon locking position (FIG. 5). Following the advancement of the cutting blade 11 towards the harvesting tip 9, the protrusion 17 slides, closing the open edge 10b of the groove 10 and defining the eyelet 18, inside of which the tendon is thus locked.

It is then possible to lock the tool in this second position, with the tendon locked inside the eyelet 18, following the activation of the locking slider 20. When the trigger 6 is rotated and brought closer to the fixed handle 5, the locking slot 22 of the trigger 6 moves into alignment with the tooth 21 of the slider 20. Since the slider 20 is spring-loaded, when the alignment between the trigger 6 locking slot 22 and the slider 20 tooth 21 occurs, the slider 20 moves forward in a distal position, pushed by the spring, towards the trigger 6, causing the tooth 21 to interfere with the trigger 6 locking slot 22, thus locking any additional trigger 6 movement.

Since the trigger 6 operates the outer movable system 13, including the blade 11, locking the trigger 6 also locks the sliding of the blade 11, which remains in the intermediate configuration for locking the tendon inside the eyelet 18 of the harvesting tip 9.

The geometric interference between slider 20 tooth 21 and locking slot 22 prevents accidental opening and closing of the handle, unless the locking slider 20 is voluntarily retracted towards the proximal end of the tool, i.e. towards the fixed handle 5. This retraction removes the geometric interference of the slider 20 with the trigger 6, thus releasing the rotation between the fixed handle 5 and trigger 6.

Figure 6:
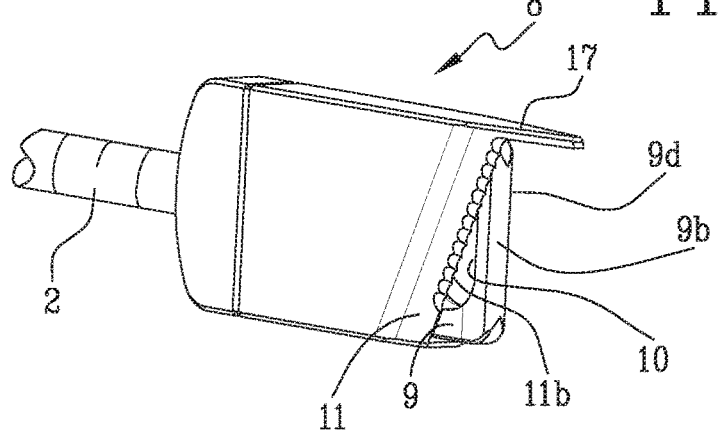
FIG. 6 is a perspective view of the portion of the cutting tool shown in FIGS. 4 and 5, in the third operating configuration as shown in FIG. 3.
Figure 7:
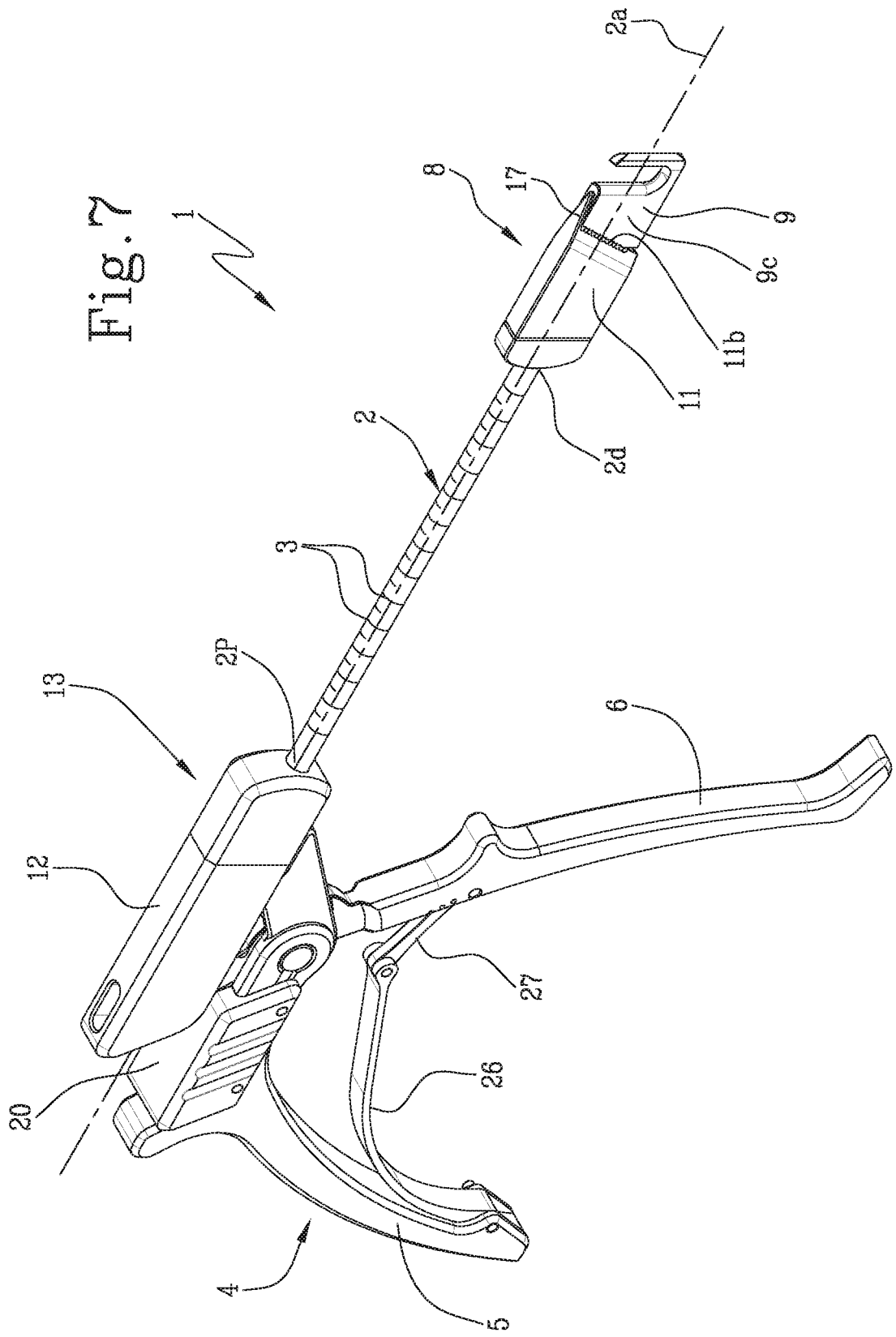
FIG. 7 is a perspective view of the cutting tool that is the subject of the present invention, in a first operating configuration.

The third configuration (FIGS. 3 and 6) involves cutting the tendon once the tool has been brought to the desired harvest depth, indicated by the graduated scale 3 on the outer lateral surface 2c of the shaft 2. By retracting the locking slider 20 to the proximal position and pressing the trigger 6, the cutting blade 11 is further advanced over the harvesting tip 9, causing the cutting edge 11a of the blade 11 to be exposed inside the eyelet 18. The further advancement of the cutting edge 11a of the blade towards the distal end 9d of the harvesting tip 9 causes the blade 11 to completely occlude the eyelet 18, resulting in a net guillotine cut of the tendon.

The angle and profile of the toothed cutting edge 11b of the blade 11 reduce resistance to cutting and enable the tendon's precise, clean removal from the end.

At this point, once the proximal end of the tendon has been severed, the tool can be removed; the tendon, which tends to contract towards its distal end due to its elasticity, is ultimately harvested and severed at the distal end, in order to be treated and implanted at another surgical site.

During operation, the tool is suitable for being handled like a gun, using the distal end 9d of the harvesting tip 9 to insert the tendon into the groove 10 of the harvesting tip 9 itself.

The grip 4 is then activated, then the trigger 6 is pressed and rotated, until the locking slider 20 advances by locking the trigger 6 and the cutting blade 11 in the second configuration, thereby locking the tendon inside the harvesting tip 9. Subsequently, the tool 1 is advanced to the desired depth guided by the graduated scale 3 on the shaft 2.

Once the desired depth has been reached, the surgeon retracts the locking slider 20 and presses the trigger 6 again to activate the outer movable system 13 and to cut the tendon.

The tool thus designed and described enables the disadvantages found in the prior art to be overcome.

In fact, the tool for the subcutaneous cutting of tendons that is the subject of the present invention is easy to use both during subcutaneous insertion and removal. The length of the surgery is thus reduced in addition to the complexity of using the tool itself.

The slider's safety system correctly locks the cutting blade of the handle, thus reducing the risk of accidentally cutting the tendon.

The blade, which is inclined with respect to the longitudinal axis of the tool, and the notched profile facilitate cutting and make it precise and accurate, significantly reducing resistance to cutting.

The tapered profile of the harvesting tip enables the soft tissue to be easily harvested and the tool to be guided as it advances.

Finally, the rounded profile of the outer edge of the distal end of the harvesting tip facilitates insertion and coupling of the tool with the tendon.

The invention claimed is:

1. A cutting tool for the subcutaneous cutting of tendons, comprising:
   a shaft arranged along a longitudinal axis, the shaft having a proximal end and a distal end;
   a grip provided at the proximal end, the grip comprising a fixed handle and a movable trigger; and
   a cutting head placed at the distal end, wherein the cutting head comprises a blade and a tendon harvesting tip provided with a groove,
   wherein said harvesting tip is tapered with respect to the longitudinal axis of said shaft,
   wherein the harvesting tip comprises a distal end, the distal end comprising an outer edge having a rounded profile,
   wherein said blade and said harvesting tip being movable relative to each other on a plane which contains the longitudinal axis of said shaft, and
   wherein said blade comprises a cutting edge that is contained in the plane, wherein first and second ends of the cutting edge lie along a rectilinear line that is inclined with respect to the longitudinal axis of said shaft as viewed in the plane.

2. The cutting tool according to claim 1, wherein said blade is slidably movable with respect to said tendon harvesting tip.

3. The cutting tool according to claim 1, wherein said shaft is integrally connected at the distal end thereof to said blade and at the proximal end thereof to a first outer connector, said first connector, said shaft, and said blade forming an outer movable system.

4. The cutting tool according to claim 3, wherein said movable trigger is connected to said first outer connector to activate said outer movable system translationally and move the blade relatively with respect to said tendon harvesting tip.

5. The cutting tool according to claim 1, wherein said shaft is a first shaft, and the cutting tool comprises a second shaft placed axially inside said first shaft, the second shaft being interposed between said grip and said cutting head, said second shaft being connected at a distal end thereof to said tendon harvesting tip and at a proximal end thereof to a second inner connector connected to the fixed handle of said grip.

6. The cutting tool according to claim 1, wherein said blade has a protrusion at one end thereof, the protrusion being adapted to close the groove of the harvesting tip while cutting a tendon.

7. The cutting tool according to claim 1, wherein the cutting tool comprises a safety device for locking the relative position between the harvesting tip and the blade.

8. The cutting tool according to claim 7, wherein said safety device comprises a locking slider sliding on said grip, the locking slider having a tooth for engaging a locking slot provided on the trigger.

9. The cutting tool according to claim 8, wherein said locking slider is loaded by a spring.

10. The cutting tool according to claim 1, wherein said trigger is rotationally connected to the fixed handle of said grip by means of a fixing joint.

11. The cutting tool according to claim 1, wherein said shaft has an external graduated scale.

12. The cutting tool according to claim 1, wherein said harvesting tip has a tapered plan profile.

* * * * *